(12) United States Patent
Storpirtis et al.

(10) Patent No.: US 6,602,991 B1
(45) Date of Patent: Aug. 5, 2003

(54) PROCESS FOR PREPARING A CHARCOAL-GM1 COMPLEX

(75) Inventors: Silvia Storpirtis, São Paulo (BR); Pedro Gonçalves De Oliveira, São Paulo (BR)

(73) Assignee: TRB Pharma Industria Quimica e Farmaceutica Ltda, Campinas (BR)

( * ) Notice: Subject to any disclaimer, the term of this patent is extended or adjusted under 35 U.S.C. 154(b) by 0 days.

(21) Appl. No.: 10/048,210

(22) PCT Filed: Jul. 27, 2000

(86) PCT No.: PCT/BR00/00083

§ 371 (c)(1),
(2), (4) Date: Jun. 5, 2002

(87) PCT Pub. No.: WO01/09151

PCT Pub. Date: Feb. 8, 2001

(30) Foreign Application Priority Data

Jul. 30, 1999 (BR) ............................................. 9903302

(51) Int. Cl.[7] ...................... A61K 31/70; A61K 31/715; C07H 15/00; C07H 15/10; C08B 37/00

(52) U.S. Cl. .......................... 536/18.5; 514/25; 514/53; 514/54; 536/4.1; 536/123; 536/124

(58) Field of Search .............................. 514/53, 54, 25; 536/4.1, 18.5, 123, 124

(56) References Cited

U.S. PATENT DOCUMENTS 4,347,244 A  8/1982  Mynard et al. ................ 514/25

FOREIGN PATENT DOCUMENTS

JP    61-012696 A    1/1986

*Primary Examiner*—Herbert J. Lilling
(74) *Attorney, Agent, or Firm*—Birch Stewart Kolasch & Birch LLP

(57) ABSTRACT

The invention provides a process to prepare a complex of adsorption charcoal-GM1 stable at different pH values. This process is based on the suspension method, the formulation example being presented. An analytical method to determine non derivatized GM1 in aqueous solutions using the high efficiency liquid chromatography technique is also object of the present invention.

2 Claims, No Drawings

PROCESS FOR PREPARING A CHARCOAL-GM1 COMPLEX

This application is the national phase under 35 U.S.C. § 371 of PCT International Application No. PCT/BR00/00083 which has an International filing date of Jul. 27, 2000, which designated the United States of America and was published in English.

TECHNICAL FIELD

This invention refers to a process for the preparation of a charcoal-GM1 complex and to an analytical method designed to determine underivatized GM1 in aqueous solutions by high performance liquid chromatography (HPLC).

This complex may be utilized as adjutant in the treatment for cholera, in the sense that it contributes to the neutralization of the correspondent toxin [STOLL et al. Lancet, p.888–891, 1980]. Moreover, in vitro tests demonstrated its potential as antidote for cases of ferrous ions intoxication.

In order to assess the effectiveness of the process for the preparation of the activated charcoal-GM1 complex, a analytical method has been developed in order to determine the GM1 by HPLC, using a new solvent system for the analysis of the ganglioside in the underivatized form.

This isocratic system has made possible the execution of the analysis with some advantages to the methodology as described in the literature.

The process for the attainment of the charcoal-GM1 complex described herein was developed seeking the stability of the product obtained in the conditions of pH as those of gastrointestinal tract, therefore helping in its safety.

BACKGROUND ART

The bacterial caused enteric infections, that result in diarrhea, dysentery and enteric fevers, accounts for serious health problems [BLACK., R. E., BROWN, K. H., BECKER, S., ALIM, A.R.M.A., HUQ, I. Am. J. Epidemiol., v. 115, p.315–324, 1982].

Among the most important pathologies of this type, we have cholera, pathology that results from the action of an enterotoxin developed from the *Vibrio cholerae* 01, a gram-negative bacteria. The production of this toxin takes place as the microorganism successfully couples with the mucous of the proximal portion of the small intestine. [LEVINE, R., KAPER, J. B., BLACK, R. E., CLEMENTS, M. L., Microbiol. Rev., v.47, n.4, p.510–550, 1983].

This toxin presents sub unity A separated from the ring plane formed by 5 minor sub units that are identical (Sub units B). Its molecular weight is of approximately 84,000, and each sub unity B has molecular weight equivalent of 11,000 and the sub unity A is divided into A1 (PM=24,000) and A2 (PM=5,000) [LEVINE, R., KAPER, J. B., BLACK, R. E., CLEMENTS, M. L. Microbiol. Rev., v.47, n.4, p.510–550, 1983].

The B pentamer is connected with GM1 ganglioside in the membrane of the intestinal epithelium cells [SUREWICZ, W. K., LEDDY, J. J., MANTSCH, H. H. Biochemistry, v.29, p.8106–8111, 1990]. The sub unity A is inserted into the cytosol, thereby liberating the A1 fragment that will activate the latent adenylate-cyclase. The result is a rapid increase in the production of the cyclical-AMP [LEVINE, R., KAPER, J. B., BLACK, R. E., CLMENTS, M. L. Microbiol. Rev., v.47, n.4, p.510–550, 1983]. The consequence of these and other factors is an excessive accumulation of salts and water in the intestinal lumen and the death of the cell [FIELD, M., RAO, M. C., CHANG, E. B., N. Engl. J. Med., v.321, p.800–806, 1989].

The ganglioside-GM1 is the specific receptor for the cholera toxin [WU, G., LEDDEN, Anal R.. Biochem., v.173, p.368–375, 1988]. Also known as monosialoganglioside, the GM1 belongs to the class of glicosphingolipids, and is differentiated (together with other gangliosides) from other components of this class by the presence of sialic acid [HADJICONSTANTIONOU, M., NEFF, N. H. J. Neurochem., v.70, n.4, p.1335–1342, 1998].

Its structure, as represented below, shows hydrophobic and hydrophilic regions. The first one consists of ceramide, constituted of sphingosine and stearic acid and the hydrophilic portion is represented by the sialoligosacaridic chain. These features may provide the formation of micelles, and it is believed that the sialic segment may be involved with the reactivity of the ganglioside with the toxin.

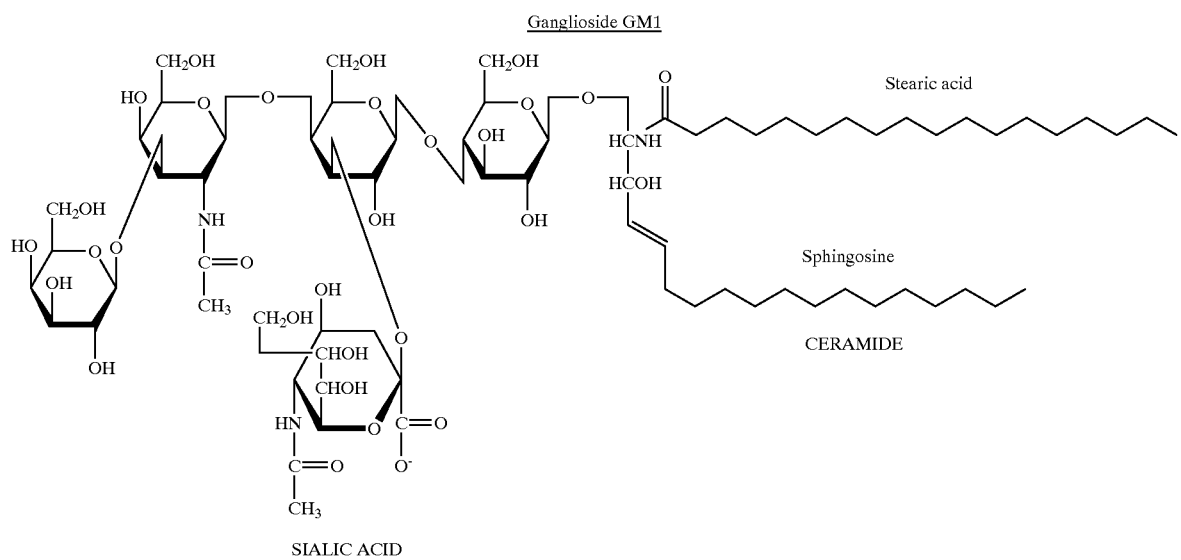

In view of its specificity by the cholera toxin, the GM1 could be used for the treatment of the toxinfection by neutralisation of the toxin in the intestinal lumen. This was originally tested with the development of the charcoal-GM1 adsorption complex by STOLL et al. [STOLL et al. Lancet, p.888–891, 1980]. Despite this, it is important to point out that the authors cite the process for obtaining this complex without, however, describing it, neither the protocol for study of stability under which the complex was submitted. There is, therefore, no description of a process for obtaining this complex in the literature, and the above work concentrates on the analysis of the therapeutic benefits made available by this complex to or for the conventional treatment of cholera.

Currently, cholera treatment covers the disinfection by antibiotictherapy, the utilization of vaccines, besides different measures for the relief of the symptoms caused by that infection. In this connection, the use of this complex accounts for an important complement for the therapy that is applied.

Aiming at the safety of the utilization of this compound, it is essential that the process used for its development results in the stability of the same under pH values that are similar to the ones found in the gastrointestinal tract. This is due, particularly to the fact that the incorporation of the GM1 in the membrane of the intestinal cells increases the biological response to the cholera toxin by an increase in the number of receptors [HOLMGREN, J., LONNROTH, J., SVENNERHOLM, L. Proc. Nat. Acad. Sci. USA 72, p.2520–2524, 1975].

For the execution of a process for the preparation of the charcoal-GM1 complex, one should obviously be certain of the quantities and degree of purity of the basic components of that complex; the charcoal and the GM1, separately.

This invention, therefore, also comprises a new method for the determination of the GM1 in aqueous solutions.

The previous technique has used HPLC, by utilizing gradient systems for elution, which at times, would generate limitations concerning the resources made available by the equipment.

Table 1 hereinbelow summarizes the methodologies described in the literature.

TABLE 1

Parameters for the chromatographic analysis of non derived gangliosides. Comparative table of analytical methodology (HPLC) as the described in the literature.

| Column (compr. × D.f. × D. part.) | Solvent System (isocratic/gradient) | λ for detection | Averaged time of analyses | Reference |
|---|---|---|---|---|
| Amine column (LiChrosorb-NH2) (25 cm × 4 mm × 7 μm) | Acetonitrile-buffer Phosphate mM, pH 5.6 (gradient) | 215 nm | 80 min. | GAZZOTI et al.[3] |
| Silicon (aquasil SS-542N) (20 cm × 6 mm × 5 μm) | n-hexano-isopropanol-potassium chloride 50 mM (gradient) | 208 nm | 25 min. | ANDO et al.[1] |
| Silicon (Aquasil SS) (20 cm × 6 mm × 5 μm) | Acetonitrile-isopropanol-potassium chloride 50 mM (gradient) | 208 nm | 30 min. | ANDO et al.[2] |
| Amine column (LiChrosorb-NH2) (25 cm × 4 mm × 5 μm) | Acetonitrile-dissodic phosphate buffered with phosphoric acid pH 5.6 (gradient) | 215 nm | 1 h 20 min. | PREVITI et al.[4] |

[1] ANDO, S., WAKI, H., KON, K. High-performance liquid chromatography of underivatized gangliosides. J. Chromatogr., Amsterdam, v. 408, p. 285–290, 1987.
[2] ANDO, S., WAKI, H., KON, K. New solvent system for high-performance thin-layer chromatography and high-performance liquid chromatography of gangliosides. J. Chromatogr., Amsterdam, v. 405, p. 125–134, 1987.
[3] GAZZOTI, G., SONNINO, S., GHIDONI, R. Normal-phase high-performance liquid chromatography separation of non-derivatized ganglioside mixtures. J. Chromatogr., Amsterdam, v. 348, p. 371–378, 1985
[4] PREVITI, M., DOTTA, M., PONTIERI, G. M., DIMARIO, U., LENTI, L., Determination of ganglio-sides by high-performance liquid chromatography with photodiode-array detection. J Chomatogr., Amsterdam, v. 605, p. 221–225, 1992.

It can be verified that the techniques indicated in the table above show times of analysis that vary from 20 minutes to 1 hour and 20 minutes. The proposed method has retention times somewhere around 8 minutes.

In addition, as can be seen from the literature describing the new method, below, this invention provides a method that was isocraticaly developed, i.e., utilizing a single mobile phase (a single composition), with relevant technical advantages.

Activated charcoal is one of the more frequently used adsorbents in medical practice, particularly in toxicology.

The pH is an important factor in its effectiveness [ROIVAS, L., NEUVONEN, P. J., J. Pharm. Sci., v.81, n.9, p.917–919, 1992], and this emphasizes the importance of verifying the behavior of this complex concerning variations of pH values and conditioning of the process for maximum effectiveness in the adsorption of the GM1.

Although the use of activated charcoal can be seen as the conduct of choice for the prevention of absorption of pharmacological agents and toxins [BYERLY, W. G., Am. Pharm., v.NS32, n.7, p.36, 1992], one of the main limitations to its antidotal activity lies in the inefficacy of adsorption of cations, for instance ferrous ions.

Accidental ingestions of preparations that contain iron are common, and this is a serious problem in pediatrics. According to ENGLE et al. [ENGLE, J. P., et al., Drug Intell. Clin. Pharm., v.21, p.153–159, 1987], approximately 2,000 cases of toxicity by iron in children are reported annually, so iron ingestion is one of the most common pediatric ingestion issues. Still according to the author, despite the frequency of poisoning by iron, there is no universally accepted protocol for cases of patients who have ingested toxic quantities of iron.

In this connection, the antidotal potential of the complex obtained by the proposed methodology, as demonstrated through in vitro tests, can account for an important alternative for cases of poisoning by ferrous ions.

DESCRIPTION OF THE INVENTION

The purpose of the invention is to provide a new process for the preparation of a charcoal-GM1 complex, characterized by the fact it comprises stages of:

(a) preparing a diluente solution (A) composed of 0 to 0.9% of sodium chloride, from 0 to 0.03% of monobasic sodium phosphate-2$H_2O$, and 0 to 0.4% of dibasic sodium phosphate-12$H_2O$, dissolved in distilled water;

(b) dissolving, in part of solution (A), sufficient amounts of GM1 that would result in concentrations that range from 0.2 to 4.0% of the ganglioside, with a new solution then obtaining (B);

(c) suspending charcoal activated in the other part solution (A) in the ratio of 1:3 to 1:7 w/v, by initiating and maintaining moderated agitation for a period of 5 to 15 minutes;

(d) slowly adding, under agitation, adequate amounts of solution (B) in order to obtain proportions that vary between 1:100 and 1:10 (GM1:charcoal), the agitation of which is maintained by a period of 10 to 20 minutes;

(e) filtering the suspension, rinsing the complex with the solution (A) and submitting it to a process of drying; and, (f) passing the dried complex through a 40 "mesh" sieve, preparing and placing the product in a hermetically locked recipient.

In a preferred embodiment, this invention is characterized by the fact that:

In stage (a), in diluente solution (A), the concentration of sodium chloride is 0.800%, and that of monobasic sodium phosphate is 0.025%, and that of dibasic sodium phosphate is 0.300%;

In stage (b), in solution (B) the concentration of GM1 in the solution (A) is of 2.000%;

In stage (c), it is suspended the activated charcoal in solution (A) in the ratio of 1:5 w/v, by initiating and maintaining moderated agitation by 15 minutes;

In stage (d), it is added, slowly and under agitation, amounts of solution "B" equivalent to the ratio 1:100 (GM1:charcoal), and the agitation should be maintained for 20 minutes; and, In stage (e) the drying up is carried out at a temperature of 40° C. during 24 hours.

The purpose of this invention is also to provide a new analytical method to determine underivatized GM1 in aqueous solutions by HPLC, characterized by the use of isocratic solvent system using a mobile phase made up of potassium chloride/acetonitrile.

In a preferred alternative for this invention method the mobile phase is made up of potassium chloride/acetonitrile of 0.1M (65:35).

Finally, this invention also comprises the study of the potential use of this complex as an antidote in intoxications by ferrous ions based on several tests conducted in vitro.

DETAILED DESCRIPTION OF THE INVENTION

Analytical Method for the Determination of GM1

The GM1 content (solution (B)) was determined by using the HPLC technique, utilizing a Hewlett-Packard chromatographer model HP 1090M series 2, equipped with Rheodyne gauge with "looping" of 250° L, and "Diode Array" detector, coupled to an acquisition system, with control and data impression. The mobile phase was made up of potassium chloride/acetonitrile 0.1M (65/35, v/v) was used a LiChrosorb column $NH_2HPLC$ (250 mm×4.6 mm×5 μm). The flow selected was of 1 mL/minute and the wave length for the detection was equivalent to 210 nm. The period for the stabilization of the equipment was 60 minutes, under analytical conditions.

The method was validated and has demonstrated sufficiently acceptable linearity (r=0.9997) in the interval of 1.50 μg and 6.04 μg of GM1, showing replicability with relative standard deviation lower than 0.700% and precision and accuracy varying between 0.230–1.280% and 97.930–103.440%, respectively (assays intra and inter-days).

The limits of detection and quantification were appropriate to the purpose proposed, with values calculated in 0.2518 μg and 0.4689±0.0265 μg of GM1, respectively.

The method developed, using an unusual solvent system for the determination of underivatized GM1, by using the high efficiency liquid chromatography technique, presents several advantages when compared to those presented in literature. Such methods use an elution gradient system and analysis time estimated between 25 and 80 minutes (Table 1), whereas the methodology proposed uses the isocratic system, with time of retention of, approximately, 8 minutes, which simplifies its execution and significantly reduces the analysis cost.

Process for the Preparation of the Charcoal-GM1 Complex

The process which is the object of the present invention comprises the following stages:

Initially, diluente solution (A) was prepared, composed of up to 0.900% of sodium chloride, up to 0.030% monobasic sodium phosphate-2$H_2O$, up to 0.400% dibasic sodium phosphate- 12$H_2O$, and the solution is completed to 100.000% with distilled water.

In this solution (A) GM1 (TRB Pharma) was dissolved, obtaining concentrations varying between 0.200% and 4.000%, which resulted in new solution (B).

In an adequate recipient, activated charcoal was suspended in a solution (A) in the proportion of 1:3–1:7 w/v, starting and maintaining moderated agitation during 5–15 minutes. After this stage, solution "B" was slowly added, under agitation. The agitation was maintained by 10–20 minutes.

The suspension was filtered using Whatman® paper filter 42, washing the complex with, approximately, 25% of the solution (A) volume.

The complex was then submitted to the process of drying (40° C./24h) and, when dried, it was passed through a sieve with 40 "mesh" and kept in hermetically sealed recipient.

Study on the Effectiveness of the Adsorption Process

The effectiveness of the process of adsorption of GM1 for the activated charcoal was checked analyzing the content of ganglioside in the filtrate. The amount of GM1 in the filtrate is inversely proportional to the effectiveness of the process.

The absence of GM1 in the filtrate, determinated according to the sensitivity of the above described method, indicates the minimum effectiveness of the complex estimated in 98%.

Study on the Stability of the Complex at Different pH Levels

Stability tests on the complex were carried out at pH levels of 1.3; 7.0 and 8.3. The complex was maintained in a suspension in the respective solutions for 20 minutes and then was filtered through paper. The assays were carried out three times and the absence of GM1 in the filtrates indicate the stability of the complex at such conditions.

A HCl solution was prepared with a pH of 1.2, adding 300 mL of the solution in 4 cubes of the solution device, which was being started using paddles.

The speed used was of 100 rpm and the average temperature was 37° C. and, once the balance of the system was established, the complex was added in 3 of the cubes of the device, the fourth cube being reserved for the addition of control charcoal.

The exposition of the complex to the acid medium was maintained, under the experimental conditions, for 20 minutes, and it was subsequently filtrated through paper.

The filtrate was submitted to the detection of GM1. The concentration of GM1 is inversely proportional to the stability of the complex.

The assay was repeated in a alkaline medium (solution of 0.18 M of $NaHCO_3$-pH=8.2) and in distilled and deaerated water.

The absence of GM1 in the filtrates resulting from this test indicates the stability of the complex in the pH values studied, in experimental conditions.

The conditions under which the complex presented best stability were:

| Diluent Solution (A): | |
|---|---|
| Sodium Chloride | 0.800% |
| Monobasic sodium phosphate -2H$_2$O | 0.025% |
| Dibasic sodium phosphate -12H$_2$O | 0.300% |
| Distilled water | q.s.p. 100% |
| Solution of GM1 (B): | |
| Ganglioside-GM1 | 2.000% |
| Diluent Solution (A) | q.s.p. 100.0% |

The activated charcoal must be suspended in solution A in the proportion of 1:5 w/v, starting and maintaining moderated agitation during 5 minutes. Solution (B) is slowly added, under agitation, according to the proportion adopted (see examples), maintaining the agitation for 20 minutes.

The suspension is filtered, washing the complex with, approximately, 25% of the solution (A) volume used in the process, submitting it to drying (40° C./24 hours). The complex should be passed through a 40 "mesh" sieve and kept in hermetically sealed recipient.

The following are examples of execution of this process. Such examples are added as illustration, but they do not limit the scope of the present invention.

EXAMPLES

The salts added aim at preventing the formation of micelles, thus, their presence may occur at variable concentrations, as exemplified in the formulae hereunder:

Example I

| Solution (A) | |
|---|---|
| Sodium chloride | 0.800% |
| Monobasic sodium phosphate 2H$_2$O | 0.025% |
| Dibasic sodium phosphate -12H$_2$O | 0.300% |
| Ganglioside GM1 | 0.020% |
| Charcoal-GM1 complex | |
| Activated charcoal | 100 parts |
| GM1 | 1 part |

Example II

| Solution (A) | |
|---|---|
| Sodium chloride | 0.800% |
| Monobasic sodium phosphate -2H$_2$O | 0.025% |
| Dibasic sodium phosphate -12H$_2$O | 0.300% |
| Ganglioside-GM1 | 0.020% |
| Charcoal-GM1 complex | |
| Activated charcoal | 50 parts |
| GM1 | 1 part |

Example III

| Solution (A) | |
|---|---|
| Sodium chloride | 0.800% |
| Monobasic sodium phosphate -2H$_2$O | 0.025% |
| Dibasic sodium phosphate -12H$_2$O | 0.300% |
| Ganglioside-GM1 | 0.020% |
| Charcoal -GM1 complex | |
| Activated Charcoal | 10 parts |
| GM1 | 1 part |

Verification on the Interaction Capacity Between Iron, the Pure Activated Charcoal and the Charcoal-GM1 Complex It was also observed that the charcoal-GM1 complex presents a potential to be used as antidote in cases of intoxication by ferrous ions.

Such conclusion comes from the result of tests carried out in vitro, according to the following description.

The methodology adopted was modified from FAVIN et al. [FAVIN, F. D. et al., Clin. Toxicol., New York, v.26, n.7, p.443–450, 1988], a solution being prepared with ferrous sulphate—7H2O, adding 2.50 g of the salt in a volumetric balloon with capacity for 1L,completing the volume with distilled water.

In 3 beckers of 250 mL, 100 mL of the obtained solution were added, adding 1.0 g of the charcoal-GM1 complex. Using FANEM magnetic agitators, the suspensions were maintained under agitation for 15 minutes, being subsequently filtered through paper. The procedure was repeated using pure activated charcoal.

The methodology mentioned above was repeated using a solution of hydrochloric acid (pH=1.2). The alkaline medium (sodium bicarbonate) was not used due to the insolubility of iron in this medium.

The filtrates were submitted to the iron analysis.

The determination of iron in the filtrates was carried out using the technique of spectrophotometry of atomic absorption. The samples were diluted for a concentration estimated between 2 ppm and 20 ppm. In fact, the samples were diluted precisely 100 times, foreseeing a maximum concentration estimated in 5 ppm.

The calibration curve was elaborated with injections of the standard solution of ferric nitrate—9H2O, whose concentration of iron varied from 2.5 ppm to 15 ppm. The linear regression analysis was carried out for obtaining the equation of the straight line. The assays were carried out in triplicata. The results are the following:

| | IRON (ppm (DPR)) | |
|---|---|---|
| | Acid (pH = 1.2) | Water |
| 0 (Control) | 554.00 (1.990%) | 439.00 (2.330%) |
| Activated charcoal | 562.00 (0.890%) | 384.00 (2.340%) |
| Charcoal-GM1 | 450.00 (0.670%) | 332.00 (3.220%) |

What is claimed is:

1. Process for preparing a charcoal-GM1 complex, characterized by comprising the stages of:
   (A) preparing a diluente solution (A) composed of 0 to 0.900% of sodium chloride, from 0 to 0.030% of monobasic sodium phosphate-2H$_2$O, and 0 to 0.400% of dibasic sodium phosphate-12H$_2$O, dissolved in distilled water;
   (b) dissolving, in part of the solution (A) from 0.200 to 4.000% of GM1, then obtaining a new solution (B);
   (c) suspending activated charcoal in the other part of the solution (A) in the proportion of 1:3 to 1:7 w/v, starting and maintaining moderated agitation for a period of 5 to 15 minutes;
   (d) slowly adding under agitation, adequate quantities of the solution (B) in such way as to obtain proportions varying from 1:100 and 1:10 (GM1:charcoal), and the agitation is maintained by a period of 10 to 20 minutes;
   (e) filtering the suspension, washing the complex with the solution (A) and submitting it to drying; and,
   (f) passing the dry complex through a 40 "mesh" sieve and storing the product in a hermetically sealed recipient.

2. Process according to claim 1, characterized by the fact that:
   in the stage (a), in the diluente solution (A), the concentration of sodium chloride is 0.800%, that of monobasic sodium phosphate is 0.025%, and that one of dibasic sodium phosphate is 0.300%;
   in the stage (b), in the solution (B), the concentration of GM1 in the solution (A) is 2.000%;
   in the stage (c), the activated charcoal is suspended in the solution (A) in the proportion of 1:5 w/v, starting and maintaining moderated agitation for 15 minutes;
   in the stage (d), quantities of the solution (B) equivalent to the proportion of 1:100 (GM1:charcoal) are slowly added, while under agitation, and the agitation is maintained by 20 minutes; and,
   in the stage (e) the drying is carried out at temperature of 40° C. for 24 hours.

* * * * *